(12) United States Patent
Amenitsch et al.

(10) Patent No.: US 9,164,047 B2
(45) Date of Patent: Oct. 20, 2015

(54) APPARATUS AND METHOD FOR SUPPORTING A LIQUID SAMPLE FOR MEASURING SCATTERING OF ELECTROMAGNETIC RADIATION

(75) Inventors: Heinz Amenitsch, Graz (AT); Benedetta Marmiroli, Modena (IT); Peter Laggner, Graz (AT)

(73) Assignee: Bruker AXS GmbH, Karlsruhe (DE)

( * ) Notice: Subject to any disclaimer, the term of this patent is extended or adjusted under 35 U.S.C. 154(b) by 164 days.

(21) Appl. No.: 13/825,993

(22) PCT Filed: Oct. 6, 2011

(86) PCT No.: PCT/EP2011/067517
§ 371 (c)(1),
(2), (4) Date: Jun. 10, 2013

(87) PCT Pub. No.: WO2012/045846
PCT Pub. Date: Apr. 12, 2012

(65) Prior Publication Data
US 2013/0259201 A1    Oct. 3, 2013

(30) Foreign Application Priority Data

Oct. 8, 2010   (EP) .................................... 10187065

(51) Int. Cl.
*G01N 23/201* (2006.01)
*H05G 1/00* (2006.01)
(Continued)

(52) U.S. Cl.
CPC .......... *G01N 23/20025* (2013.01); *G01N 21/51* (2013.01); *G01N 23/2204* (2013.01)

(58) Field of Classification Search
CPC .......... G01N 23/20025; G01N 23/203; G01N 23/04; G01N 21/51; G01N 23/2204; G01N 2223/076; G01N 23/223; G01N 2223/637; Y10T 428/2982; Y10T 29/301; Y10T 29/49938; Y10T 436/143333; Y10T 436/153333; Y10T 436/11; Y10T 436/117497; Y10T 117/1004; Y10T 117/1024; Y10T 137/2224; Y10T 137/87652; Y10T 29/49108; Y10T 307/305; Y10T 307/50; G02B 27/48; G02B 19/0014; G02B 19/0052; G02B 19/0085; G02B 19/009; G02B 19/0095; G02B 26/10; G02B 27/095; G06K 7/10594; G06K 9/26; G06K 9/325; G06K 7/10732
USPC .............................................. 378/86, 70, 208
See application file for complete search history.

(56) References Cited

U.S. PATENT DOCUMENTS 4,975,217 A   12/1990   Brown-Skrobot
5,350,697 A    9/1994   Swope
(Continued)

FOREIGN PATENT DOCUMENTS

EP          1 477 796       11/2004
WO       WO 98/41323       11/1998
(Continued)

*Primary Examiner* — Irakli Kiknadze
(74) *Attorney, Agent, or Firm* — Paul Vincent

(57) ABSTRACT

An apparatus for supporting a liquid sample for measuring an intensity of X-ray radiation scattered by the liquid sample is configured such as to allow the X-ray radiation to impinge along a first direction (117, 217, 317, 417, 517, 617) through the first support member onto the liquid sample and to leave the liquid sample through the second member along a second direction (119, 219, 319, 419, 519, 619) different from the first direction to be detected by a detector. Further, a system for measuring an intensity of X-ray radiation scattered by a liquid sample and corresponding methods are provided.

13 Claims, 3 Drawing Sheets

(51) Int. Cl.
*G01N 23/20* (2006.01)
*G01N 21/51* (2006.01)
*G01N 23/22* (2006.01)

(56) References Cited

U.S. PATENT DOCUMENTS

| | | | |
|---|---|---|---|
| 5,406,087 A | 4/1995 | Fujiyoshi | |
| 2002/0140931 A1 | 10/2002 | Robertson | |
| 2002/0154299 A1 | 10/2002 | Robertson | |
| 2002/0176536 A1* | 11/2002 | Ayukawa et al. | 378/66 |
| 2006/0032433 A1* | 2/2006 | Sakata | 117/89 |
| 2006/0261284 A1 | 11/2006 | Chao | |
| 2008/0002181 A1 | 1/2008 | Robertson | |
| 2009/0086198 A1 | 4/2009 | Gotschy | |
| 2010/0193398 A1 | 8/2010 | Marsh | |
| 2011/0243301 A1* | 10/2011 | Watanabe et al. | 378/46 |

FOREIGN PATENT DOCUMENTS

| | | |
|---|---|---|
| WO | WO 2007/131945 | 11/2007 |
| WO | WO 2010/100502 | 9/2010 |

* cited by examiner

APPARATUS AND METHOD FOR SUPPORTING A LIQUID SAMPLE FOR MEASURING SCATTERING OF ELECTROMAGNETIC RADIATION

This application is the national stage of PCT/EP2011/067517 filed Oct. 6, 2011 and also claims Paris convention priority of EP 101 870 65.7 filed Oct. 8, 2010.

BACKGROUND OF THE INVENTION

The present invention relates to an apparatus and to a method for supporting a liquid sample for measuring an intensity of X-ray radiation scattered by the liquid sample. Further, the present invention relates to a system for measuring an intensity of X-ray radiation scattered by a liquid sample. In particular, the present invention relates to an apparatus and to a method for supporting a liquid sample for measuring an intensity of X-ray radiation scattered by the liquid sample, wherein the liquid sample is supported between two surfaces facing each other and supporting the liquid sample purely by a surface tension force. In particular, the electromagnetic radiation may be X-ray radiation, wherein, small angle X-ray scattering (SAXS), and/or wide angle X-ray scattering (WAXS) may be employed.

EP 1 477 796 A2 discloses a small angle X-ray scattering system with the X-ray beam oriented vertically for simplified analysis of liquid samples, wherein the sample is placed on a thin sample support, such as a piece of polyester film. Thereupon, the liquid sample is held and spreads naturally under the force of gravity.

The publication "High-Throughput Small Angle X-ray Scattering from Proteins in Solution Using a Microfluidic Front End", Analytical Chemistry, 2008, 80, 3648-3654, by K. N. Toft et al. discloses a microfluidic system with sample and buffer inlets, mixing channel and sample chamber for measuring small angle X-ray scattering from a sample placed in the sample chamber. Thereby, the sample chamber comprises polystyrene (PS) enclosing the sample completely. An advantage of the microfluidic device employed in a scattering experiment may be that the sample conditions may be modified in situ. On the other hand, the surface to volume ratio is big resulting in a strong interference of a signal from the channel walls with a signal from the sample. In particular, the sample may be deposited or may sediment on the walls of the microfluidic device and may change the real concentration of the constituents of the sample (which may partially adhere to the channel walls of the microfluidic device). Moreover, in most cases filling of the channels requires pumping the fluid sample involving applying a shear stress to the sample. This may perturb or even damage especially a biological sample.

Alternatively, a liquid sample may be placed into a standard array of wells or of capillaries with an automatic sample changer for measuring X-ray scattering data. Typically, these automatic sample changers manipulate volumes of sample which are bigger than 1 µl or even bigger than 10 µl. Moreover, using syringes presents the same problems as the pumping of the sample when using microfluidic devices: The sample is subjected to shear stress with the risk of damaging or at least modifying the sample, in particular a sensible biological sample. Further, the true concentration of constituents, such as proteins, in the sample may be changed due to specific adsorption of specific constituents to a well wall or to a wall of a syringe.

There may be a need for an apparatus and for a method for supporting a liquid sample for measuring an intensity of X-ray radiation scattered by the liquid sample which allows very small sample volumes, such as in the microliter or nanoliter range, which reduces a contact area between a support and the sample, which reduces shear forces experienced by the sample, which reduces sample loss, which allows a fast measurement, which allows easy cleaning of the support and/or which allows easy coupling with an automatic sample changer.

Further, there may be a need for a system for measuring an intensity of X-ray radiation scattered by a liquid sample providing at least one of the above-mentioned advantages.

SUMMARY OF THE INVENTION

According to an embodiment an apparatus for supporting a liquid sample for measuring an intensity of X-ray radiation scattered by the liquid sample is provided, wherein the apparatus comprises a first support member (in particular being transparent to the X-ray radiation, such that at least in a portion of the first support member an attenuation of the X-ray radiation transmitted through the first support member is less than 50%, in particular less than 30%, further in particular less than 10%) having a first surface (which may have any surface shape, being in particular curved or flat); a second support member (in particular being transparent for the X-ray radiation transmitted through the second support member such that an attenuation of the X-ray radiation transmitted through the second support member is less than 50%, in particular less than 30%, further in particular less than 10% in at least a portion of the second support member) having a second surface (being of any shape, being in particular curved or plane or flat), the first surface and the second surface being adapted such that the liquid sample (which may have a volume in the microliter range or nanoliter range, such that the volume may be in a range between 1 nl and 10 µl, in particular in a range between 10 nl and 1 µl, further in particular in a range between 100 nl and 500 nl) is supportable between the first surface and the second surface (which may be arranged in particular opposite to each other, in particular parallel to each other) by a surface tension force (comprising e.g. a surface tension force between the liquid sample and the first surface, a surface tension force between the liquid sample and the second surface, a surface tension force between the liquid sample and an ambient atmosphere, a surface tension force between the ambient atmosphere and the first surface, and a surface tension force between the ambient atmosphere and the second surface), wherein the apparatus is configured such as to allow the X-ray radiation (in particular X-ray radiation in particular having an energy between 5 keV and 80 keV, in particular having an energy of at least approximately 8 keV) to impinge along a first direction (in particular being transverse to at least one of the first surface and the second surface, in particular being at least approximately perpendicular to the first surface and/or to the second surface) through the first support member (in particular along a thickness direction of the first support member being perpendicular to the first surface) onto the liquid sample (in particular a solution (water based, in an inorganic solvent and/or organic solvent based) or a dispersion of substances, molecules and/or particles in water, in an inorganic solvent and/or in an organic solvent) and to leave the liquid sample (after scattering the X-ray radiation at molecules, substances, or particles or solute molecules or substances contained in the liquid sample) through the second member (in particular in a direction transverse to the second surface which must not necessarily be along the thickness direction of the second member) along a second direction different from the first direction to be detected by a detector.

In particular, the liquid sample may contact both the first surface and the second surface, in particular thereby wetting the first surface as well as the second surface. In particular, the first surface and the second surface may at least in a portion thereof be hydrophilic, such that a water-based sample wets the first surface as well as the second surface, if the liquid sample is an aqueous solution. In particular, the first surface and the second surface may at least in a portion thereof be solventphilic, such that an in-/organic solvent-based sample wets the first surface as well as the second surface, if the liquid sample is an in-/organic solvent-based solution.

In particular, the first support member and the second support member are separate items, wherein a clearance is present between the first support member and the second support member. In particular the fluid sample may be in contact with a solid structure only via the first surface and the second surface and the liquid sample may comprise an annular surface between the first surface of the first support member and the second surface of the second support member, wherein this annular surface of the liquid sample may be in contact with a gas atmosphere which does not have a supporting function. Thus, the liquid sample may be exclusively supported by a surface tension force established at the first surface and the second surface.

Thereby, an apparatus for measuring the scattering of X-ray radiation of a liquid sample in form of small drops in the microliter or nanoliter range is provided. Thereby, the sample is held by a surface tension force between the first surface and the second surface, wherein these two surfaces may be arbitrarily arranged vertically or horizontally or in any other configuration depending on the direction of the impinging X-ray radiation (also referred to as primary X-ray radiation or primary beam). In particular, the scattering may comprise Small Angle X-Ray Scattering (SAXS) and/or Wide Angle X-Ray Scattering (WAXS). In particular, the first surface and the second surface between which the drop or the liquid sample is held may or may not be parallel and/or flat.

In particular, the first support member and the second support member may be translatable or rotatable for moving or rotating the liquid sample supported between the first surface and the second surface.

The first surface (and/or the first support member) may comprise an X-ray transparent window (e.g. diamond or $Si_3N_4$), which may allow the scattered radiation to leave along the second direction. In particular, at least one of the first support member and the second support member may be movable (relative to the other) for example for adjusting a distance between the first surface and the second surface and/or for loading the sample, and/or cleaning the first surface and/or the second surface. In particular, the first surface and the second surface may be held in a container enclosing a gas atmosphere, in particular an air atmosphere which may be controlled regarding its solvent vapour pressure, regarding its temperature and/or regarding its pressure. Further, a microscope or a camera may be provided for observing the sample. In particular, the sample may be loaded or fed or placed between the first surface and the second surface manually and/or automatically via a feeding robot through standard or custom-made dispensing systems. The container in which the first surface and the second surface are installed may be put in vacuum to reduce attenuation of the X-rays, during the measurement. The X-rays (the primary X-ray radiation as well as the secondary X-ray radiation representing the X-ray radiation scattered by the liquid sample) may pass the liquid sample drop across the first surface and the second surface between which the drop is held.

In particular, the apparatus may be employed for characterizing nanostructures in the liquid sample in solution. The liquid sample may in particular include nucleic acids, proteins, liposomes, nanoparticles and/or drugs dissolved in water and/or dissolved in an in-/organic solvent. In particular, placing and supporting the liquid sample between the first surface and the second surface may reduce sample loss and may reduce distortion of a concentration of substances dissolved in the solvent due to extensive adsorption to walls of a support structure, such as a sample chamber.

In particular, the apparatus for supporting a liquid sample for measuring an intensity of X-ray radiation may comprise, according to an embodiment, a primary X-ray path for allowing the primary X-ray radiation to impinge onto the liquid sample along the first direction and a secondary X-ray path for allowing the secondary X-ray radiation scattered by the liquid sample to leave the liquid sample along the second direction being different from the first direction. The primary and/or secondary path may comprise a tubing system and may be evacuated to reduce attenuation.

In particular, the first direction may include an angle ($\alpha$) with the second direction which is greater than 0°, in particular greater than 1°, further in particular greater than 3°, even further in particular greater than 5°. In particular, a wavelength of the scattered X-ray radiation may at least approximately be equal to a wavelength of the primary X-ray radiation impinging onto the liquid sample. In particular, the liquid sample may spread across the first surface and the second surface forming a wetted area on the first surface and the second surface, wherein the wetted area is in particular larger than a cross-sectional size of the impinging primary beam. In particular, an area size of the first surface may be different from an area size of the second surface.

According to an embodiment the second direction and the first direction include an angle ($\alpha$) between 0.1° and 90°, in particular between 2° and 60°, further in particular between 5° and 40°, further in particular between 7° and 35°. In particular, when employing small angle X-ray scattering the angle $\alpha$ may be ranged between 0° and 9°, in particular between 0.06° and 8°. In particular, when performing wide angle X-ray scattering the angle $\alpha$ may range in between 16° and 27° according to an exemplary embodiment.

According to an embodiment the first surface can be a plane surface (i.e. comprises at least a portion which is flat having no curvature) in at least a first region where the X-ray radiation impinges onto the first member and/or the second surface can be a plane surface in at least a second region where the X-ray radiation leaves the second member. Thereby, a manufacture of the first support member and/or the second support member may be simplified.

According to an embodiment the first direction is transverse, in particular at least approximately perpendicular, to at least one of the first surface and the second surface. Thereby the primary X-ray radiation may travel along a thickness direction of the first support member and/or (at least approximately) along a thickness direction of the second support member. Thereby, a transmission path length of a transmission of the primary X-ray radiation through the first support member and/or through the second support member may be optimized for the efficiency of the measuring experiment and/or required sample volume.

According to an embodiment the second surface has a larger area size than the first surface. Thereby, it may be allowed that the scattered X-ray radiation which has spread due to the scattering may transmit the second surface without being blocked by a too small second surface area size. In contrast, the area size of the first surface may correspond to (or be larger than or at least equal to) a beam cross-sectional size of the X-ray radiation which may amount to between 1 μm×1 μm (1 μm=1 micrometer) to 5 mm×5 mm.

According to an embodiment the second surface is curved, in particular concavely curved. Thereby, the scattered X-ray radiation travelling along a number of different directions, each one being different from the first direction may travel through the second support member on a path having a smaller path length than a path, when the second surface would be flat or plane. Thereby, an attenuation of the scattered X-ray radiation may be reduced, thus improving the sensitivity of the apparatus, when employed for performing a scattering measurement. According to an embodiment at least one of the first surface and second surface is convexly curved, wherein the sample is placeable between the first surface and second surface in a region having a smallest distance from each other.

According to an embodiment the first member and/or the second member comprises a plate, the plate in particular comprising diamond and/or silicon nitride. Thereby, the manufacturing the first member and/or the second member may be facilitated, wherein the first member and/or the second member may be transparent to X-ray radiation.

The essential criteria for the choice of x-ray windows are high transparency for X-rays, low X-ray scattering and mechanical stability against a pressure difference of 1 bar. High transparency is achieved by minimum thickness, and therefore monocrystalline materials like diamond and $Si_3N_4$ have particular advantages since they are available at micrometer and submicrometer thicknesses with areas of larger than 1 $\mu m^2$ as required for the present purpose. Both materials have been widely proven as excellent candidates for X-ray windows in the demanding environment of synchrotron radiation.

According to an embodiment the liquid contacts the first surface at a first wetted area of the first surface and contacts the second surface in a second wetted area of the second surface. In particular, the first surface may be hydro-/solventphilic at the first wetted area and the second surface may be hydro-/soventphilic at the second wetted area such that the liquid sample (in particular an aqueous solution) spreads at least across the first wetted area and the second wetted area. Thereby, a "hydrophilic surface" may denote a surface which may be charged-polarized and may be capable of hydrogen bonding, enabling the hydrophilic surface to be wetted more readily by water than by oil or by other hydrophobic solvents. In particular, the hydrophilic surface may comprise alcohol chains. Thereby, when the liquid sample is an aqueous solution it may readily spread over the first surface and the second surface in at least the first wetted area and the second wetted area for improving the support of the liquid sample.

According to an embodiment around the first wetted area of the first surface a first surrounding area of the first surface is hydro-/solventphobic and/or around the second wetted area of the second surface a second surrounding area of the second surface is hydro-/solventphobic. A "hydro-/solventphobic surface" may be repelled from water/solvent. In particular, a hydrophobic surface may comprise non-polar molecules and may prefer neutral molecules or non-polar solvents to be in contact with the hydrophobic surface. Examples of hydrophobic molecules include the alkanes, oils, fats and greasy substances in general.

Depending on the presence of a hydro-/solventphilic portion and/or a hydro-/solventphobic portion at the first surface and the second surface a contact angle i.e. wetting conditions of the liquid sample supported by the first surface and the second surface may be established reflecting a configuration, wherein surface forces, in particular surface tension forces, and the gravity forces of the droplet are in balance and the droplet is held in a stable configuration allowing the direct beam and the scattered beam pass entirely through the droplet held firmly between the foreseen window areas of the first and the second surface. Adjustment of the hydro-/solventphilicity and/or hydro-/solventphobicity of the first surface and the second surface (in particular in different portions thereof) may allow adjustment of an appropriate contact angle i.e. surface tension forces of the liquid sample placed on the first surface and the second surface. Further, this kind of adjustment may also allow adjustment of a supporting force for supporting the liquid sample between the first surface and the second surface.

According to an embodiment the first wetted area of the first surface and the second wetted area of the second surface have a distance from each other between 0.1 mm and 3 mm, in particular between 0.2 mm and 2 mm, further in particular between 0.5 mm and 1 mm. Thereby, a liquid sample having a small volume, such as in the nanoliter or microliter range, may be advantageously supported between the first surface and the second surface. Further, the distance between the first surface and the second surface may be adjustable to allow adjustment of a volume or volume thickness subjected to or interacting with the primary X-ray radiation. In particular, for a stronger scattering liquid sample the distance between the first surface and the second surface may be adjusted to be smaller than for a weakly scattering liquid sample.

According to an embodiment the apparatus for supporting a liquid sample for measuring an intensity of X-ray radiation scattered by the liquid sample further comprises a container wall enclosing a gas atmosphere, wherein the fluid sample comprises an annular surface between the first surface and the second surface, wherein this annular surface is in contact (in particular in communication) with the gas atmosphere. Thus, the liquid sample is not supported at the annular surface by any solid support structure. The annular surface may be convex, when the contact angle between the liquid sample and the first surface or the second surface is larger than 90° and may be concave, when the contact angle between the liquid sample and the first surface and the second surface is less than 90°. According to an embodiment the annular surface of the liquid sample is convex/concave. In that the liquid sample is in communication and in contact with the gas atmosphere it is enabled, to control the solvent content of the liquid sample, in particular avoiding drying-out the liquid sample.

According to an embodiment the apparatus for supporting a liquid sample further comprises a humidity/solvent vapor pressure control system for controlling a humidity/solvent vapour pressure of the gas atmosphere and/or comprising a temperature control system for controlling a temperature of the gas atmosphere and/or controlling a temperature of the first support member and/or the second support member. In particular, the gas atmosphere may be an air atmosphere having an adjustable temperature and having an adjustable humidity/solvent vapor pressure. Thereby, a liquid sample in an adjustable condition and in a changeable condition (changeable state) may be measured. In particular, the temperature control system may comprise a Peltier module or one or more Peltier modules to change the temperature of the gas atmosphere. In particular, the container may support the first support member and the second support member, for example using a frame structure. The top of the container may be opened and may have a (closable) aperture which can fit with standard dispensing pipette tips. The temperature control system may be placed outside the container. Further, the container may comprise an (closeable) outlet to discharge the liquid sample after measurement and after cleaning the first surface and the second surface. The inside part of the container may be covered with a hydro-/solventphobic coating. Further, according to an embodiment, the apparatus for supporting a liquid sample may comprise an automatic sample filler, e.g. composed of a robot which may handle the system for dispensing the sample and for cleaning.

According to an embodiment a system for measuring an intensity of X-ray radiation scattered by a liquid sample is provided, wherein the system comprises an apparatus according to an embodiment of an apparatus for supporting a liquid sample as described above and a detector configured for detecting the intensity of the X-ray radiation impinged along the first direction through the first support member onto the liquid sample and having left the liquid sample through the second member along the second direction. The detector may comprise one or more detector elements for resolving portions of the (intensity of the) X-ray radiation scattered at different scattering angles. According to another embodiment, the detector may be placed at a fixed angle $\alpha$ being offset from (not in line with) the first direction (the impinging direction of the primary X-ray radiation). The detector may be adapted for detecting an intensity of X-ray radiation impinging on the one or more detector elements. Further, the detector may comprise a beam stop for blocking or at least attenuating the primary X-ray radiation impinging along the first direction.

According to an embodiment the container comprises an opening which is in particular closeable. In particular the opening may be a closeable aperture or a closeable outlet for sample loading or sample cleaning.

According to an embodiment the system for measuring an intensity of X-ray radiation scattered by a liquid sample comprises a detector which is adapted for detecting at least one of small angle X-ray scattering from the liquid sample, wide angle X-ray scattering from the liquid sample, resulting from the impingement of the X-ray radiation onto the liquid sample. This non-invasive method may have an advantage of high precision and fast response time.

For X-ray measurements (such as SAXS, WAXS) an X-ray source may be provided to generate a primary X-ray beam (primary X-ray radiation) which may be directed horizontally, vertically or in any arbitrary inclination along a primary beam path to the liquid sample located between the first surface and the second surface. The small and wide angle scattered X-ray, respectively, may travel through a secondary beam path to the detector. The primary beam path and also the secondary beam path may be evacuated and separated from the container in which the liquid sample is supported by the first surface and the second surface. Beam conditioning optics and one or more collimators may be used in the primary beam path and in particular a beam stop may be used in the secondary beam path to block transmitted X-rays. The X-ray source may be any available source (e.g. X-ray tube, synchrotron light, free electron laser source or compact light sources).

Small angle X-ray scattering may in particular be used for the study of the liquid sample (and the constituents contained in the liquid sample) in a spatial range from about 1 nm to 1000 nm. Wide angle X-ray scattering may be employed in a range from 0.1 nm to 1 nm of object size. Together (in particular in combination) SAXS/WAXS may provide information about size, shape, volume fraction, inner structure and interactions of colloids, polymers and biological samples.

Features (individually or in any combination) which have been disclosed, described or explained with respect to an apparatus for supporting a liquid sample for measuring an intensity of X-ray radiation or a system for measuring an intensity of X-ray radiation scattered by a liquid sample may also be applied to a method for supporting a liquid sample for measuring an intensity of X-ray radiation scattered by the liquid sample and vice versa (individually or in any combination).

According to an embodiment a method for supporting a liquid sample for measuring an intensity of X-ray radiation scattered by the liquid sample is provided, wherein the method comprises providing a first support member having a first surface; providing a second support member having a second surface; supporting the liquid sample between the first surface and the second surface by a surface tension force; arranging the first member and the second member such as to allow the X-ray radiation to impinge along a first direction through the first support member onto the liquid sample and to allow the X-ray radiation scattered by the liquid sample to leave the liquid sample through the second member along a second direction different from the first direction to be detected by a detector.

In particular, the method may further comprise arranging a primary beam path such as to allow the X-ray radiation to impinge along the first direction through the first support member onto the liquid sample and may also comprise arranging a secondary beam path such as to allow the X-ray radiation scattered by the liquid sample to leave the liquid sample to the second member along the second direction. The primary beam path and/or the secondary beam path may be evacuated.

Embodiments of the present invention are now described with reference to the accompanying drawings. Thereby, the drawings are not necessarily to scale. Like reference signs denote elements which are alike in structure, function and/or purpose throughout the drawings.

DESCRIPTION OF THE PREFERRED EMBODIMENT

Figures 1A, 1B:
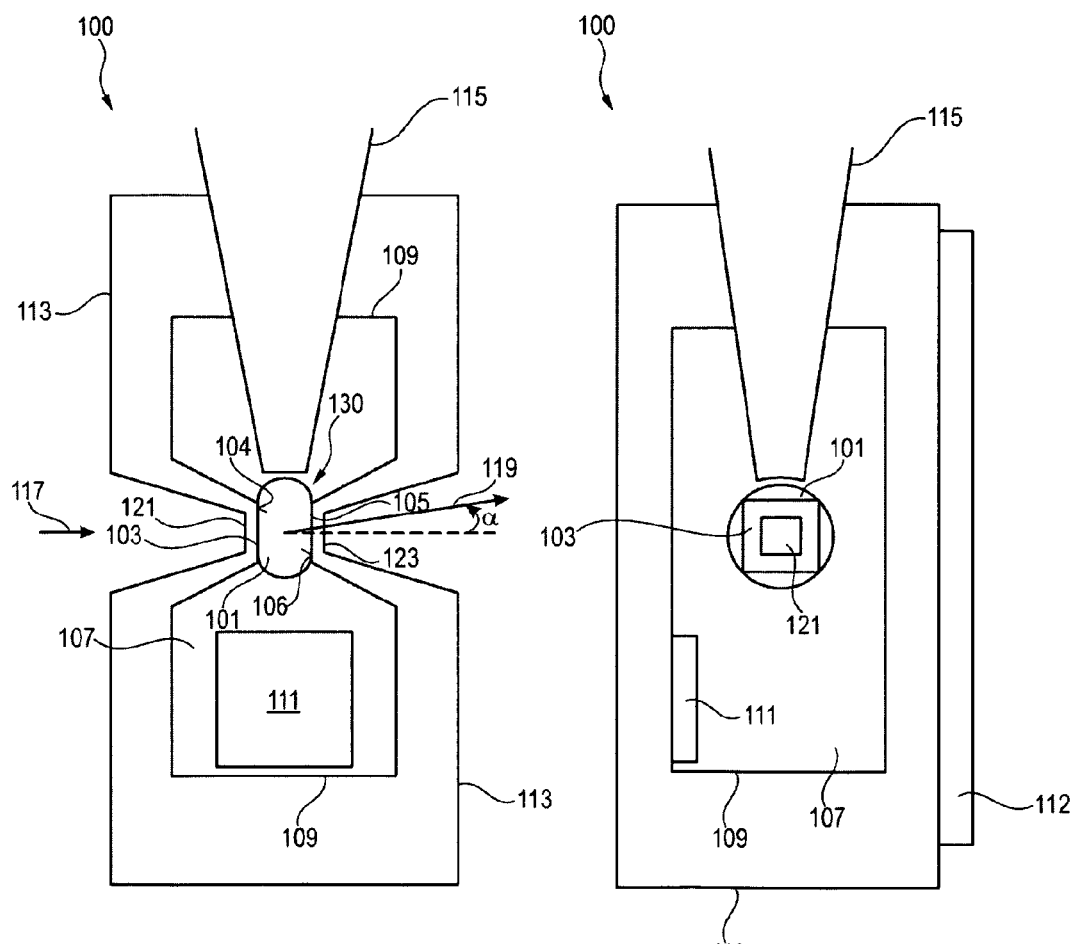
FIGS. 1A and 1B schematically illustrate an apparatus for supporting a liquid sample according to an embodiment.

FIGS. 1A and 1B illustrate a front view and a side view, respectively, of an embodiment of an apparatus 100 for supporting a liquid sample. The apparatus 100 for supporting a liquid sample 101 comprises a first support member 103 having a first surface 104 and a second support member 105 having a second surface 106. The fluid sample 101 is placed between the first surface 104 and the second surface 106 and is held by a surface tension force established between the first surface 104 and the liquid sample 101, the second surface 106 and the liquid sample 101, a gas atmosphere 107 and the liquid sample 101, between the gas atmosphere 107 and the first surface 104, and between the gas atmosphere 107 and the second surface 106.

The liquid sample 101 has a volume between 10 nl and 10 µl. The first support member 103 as well as the second support member 105 comprise e.g. a glass plate, mica, polymer foils/films, LiF, sapphire, a diamond plate, or a silicon nitride plate.

Thereby, the first surface 104 is a substantially flat surface being parallel to the substantially flat surface 106. The gas atmosphere 107 is enclosed by a container wall 109 which also encloses a humidity/solvent vapor pressure sensor 111 for sensing and controlling a humidity/solvent vapor pressure within the gas atmosphere 107. Alternatively specific solutions can be introduced to establish specific solvent vapor pressures passively. A Peltier module 112 allows control of the temperature of the atmosphere 107. The container wall 109 forms a container filled with the gas atmosphere, wherein the container including the first support member 103 and the second support member 105 is encased by a casing 113. The casing 113 and also the container enclosed by the container wall 109 may be opened to load the liquid sample 101 between the first surface 104 and the second surface 106 using a pipette tip 115, as depicted in FIGS. 1A and 1B. The casing 113 and also the container enclosed by the container wall 109 may be opened at bottom or have an appropriate opening at the bottom for cleaning and sample disposal.

The apparatus 100 for supporting the liquid sample 101 may be arranged such that an X-ray beam, impinges along a first direction 117 through the first support member 103, to be scattered within the liquid sample 101 and to leave the liquid sample 101 through the second support member 105 along a second direction 119 including an angle α with the first direction 117 which is larger than 0.

FIG. 1B schematically illustrates the apparatus 100 depicted in FIG. 1A in a side view such that the first direction 117 (the direction of the primary X-ray radiation) is perpendicular to the drawing plane. The primary X-ray radiation 117 enters through a window 121 of the casing 113 and exits through a window 123 the casing 113. After entering through the window 121, the primary X-ray radiation travelling along the direction 117 passes through the first support member 103 to interact with the liquid sample 101 supported by a surface tension force between the first surface 104 of the first support member 103 and the second surface 106 of the second support member 105. For loading the liquid sample 101 the first support member 103 and the second support member 105 may be movable relative to each other. The secondary X-ray radiation scattered in a direction 119 is detected by a (not illustrated) detector.

Figures 2A, 2B, 2C:
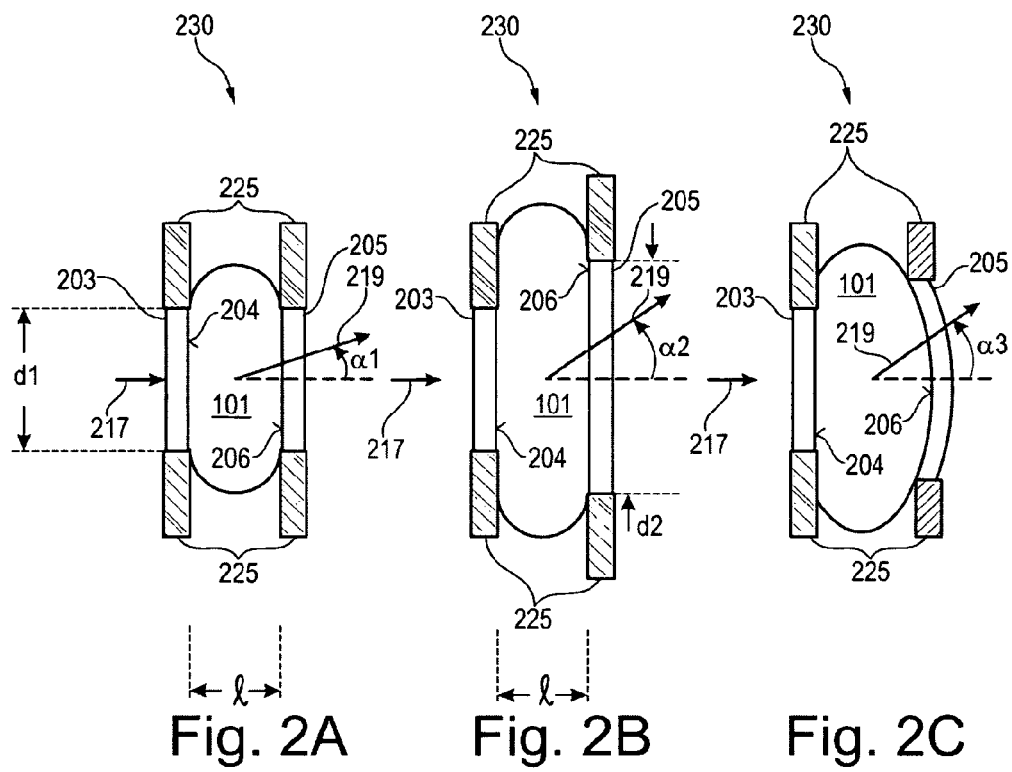
FIGS. 2A, 2B, 2C, 2D, 2E schematically illustrate a side view of supporting members for supporting a liquid sample for measuring an intensity of X-ray radiation scattered by the liquid sample according to embodiments.

FIGS. 2A, 2B and 2C illustrate different embodiments of a support structure 230 comprising a first support member 203 and a second support member 205 for supporting the liquid sample 101.

The embodiment of the support structure 230 illustrated in FIG. 2A comprises a first support member 203 and a second support member 205 being formed by flat plates which are transparent to the X-ray radiation impinging in a direction 217 and leaving the support structure after being scattered by the liquid sample in a direction 219. The first surface 204 of the first support member 203 is spaced apart from the second surface 206 of the second support member 205 by a distance I which may amount to between 10 μm and 1 cm. The first support member 203 as well as the second support member 205 is held by a frame 225. In particular, the frame structure 225 is not transparent to the X-ray radiation. A free characteristic dimension d of a transparent area of the first support member 203 and the second support member 205, which both could have an arbitrary shape, e.g. circular, elliptical, rectangular, may range between 1 μm and 1 cm.

FIG. 2B schematically illustrates another embodiment of a support structure 230 comprising a first support member 203 and a second support member 205 which are arranged parallel to each other spaced apart by a distance I. As in the embodiment of the support structure 230 illustrated in FIG. 2A the first support member 203 and the second support member 205 comprise flat plates which are supported by a frame structure 225 being not transparent to the X-ray radiation. In contrast however to the embodiment illustrated in FIG. 2A the support structure 230 illustrated in FIG. 2B comprises a second support member 205 which has a larger dimension d2 than the dimension d1 of the first support member 203. Thereby, X-ray radiation scattered by an angle α2 may leave the support structure 230 to be detected by a detector, wherein the scattering angle α2 is larger than the scattering angle α1 of the embodiment illustrated in FIG. 2A. Thus, the embodiment of a support structure 230 illustrated in FIG. 2B is suitable for experiments employing scattering at wider angle, such as wide angle X-ray scattering experiments.

FIG. 2C illustrates another embodiment of a support structure 230. While the first support member 203 comprises a flat plate as in the embodiments illustrated in FIGS. 2A and 2B the second support member 205 illustrated in FIG. 2C has a curved shape, wherein in particular the second surface 206 has a concave shape which also allows that scattered X-ray radiation scattered at a higher angle α3 leaves the support structure 230 to be detected by a detector. Further, the second support member 205 is supported by a frame structure 225.

Figures 2D, 2E:
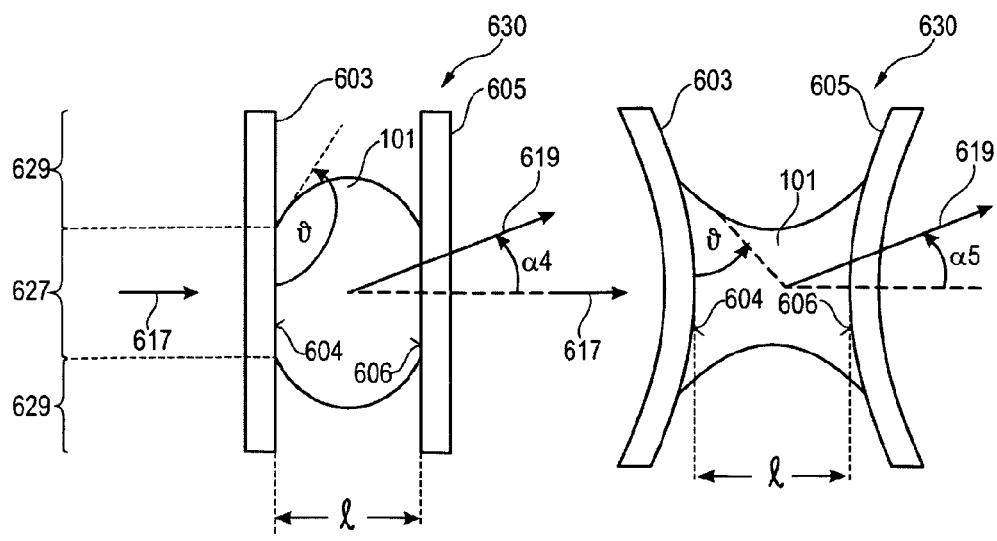

FIGS. 2D and 2E illustrate further embodiments of a support structure 630 comprising a first support member 603 and a second support member 605 for supporting the liquid sample 101.

The embodiment of the support structure 630 illustrated in FIG. 2D comprises a first support member 603 and a second support member 605 being formed by flat plates which are transparent to the X-ray radiation impinging in a direction 617 and leaving the support structure after being scattered by the liquid sample in a direction 619. The first surface 604 of the first support member 603 is spaced apart from the second surface 606 of the second support member 605 by a distance I. The sample 101 is arranged between the first surface 604 and the second surface 606 and contacts both, wherein a contact angle σ (which is larger than 90°) is established by a balance of surface tension forces. In a region 627 the first surface 604 and the second surface 606 are hydrophilic by appropriate coating and in a region 629 surrounding the region 627 the first surface 604 and the second surface 606 are hydrophobic by appropriate coating resulting in the contact angle as illustrated and in a confinement of the sample to be centered at the region 617.

The embodiment of the support structure 630 illustrated in FIG. 2E comprises a first support member 603 and a second support member 605 being formed by curved plates which are transparent to the X-ray radiation impinging in a direction 617 and leaving the support structure after being scattered by the liquid sample in a direction 619. The first surface 604 of the first support member 603 is concave and is spaced apart from the second concave surface 606 of the second support member 605 by a distance I at a vertical position of closest approach. The sample 101 is arranged between the first surface 604 and the second surface 606 and contacts both, wherein a contact angle σ (which is smaller than 90°) is established by a balance of surface tension forces. The first surface 604 and the second surface 606 are hydrophilic by appropriate coating throughout their entire extent and the liquid sample is confined close to the region of closest approach of the two surfaces 604 and 606 by surface tension forces.

Figure 3:
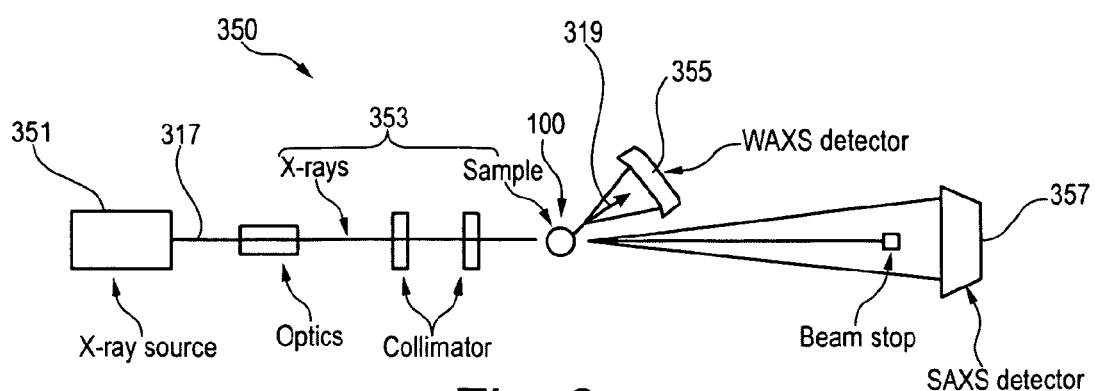
FIG. 3 schematically illustrates an embodiment of a system for measuring an intensity of X-ray radiation scattered by a liquid sample, wherein small angle or wide angle X-ray scattering is applied.

FIG. 3 schematically illustrates a system 350 for measuring an intensity of X-ray radiation scattered by a liquid sample, which is suitable for performing at least one of small angle X-ray scattering and wide angle X-ray scattering. The system 350 comprises an X-ray source 351 for generating a primary X-ray beam travelling along a direction 317. The X-ray beam travelling along the direction 317 is shaped using optics and collimators 353 to impinge onto an apparatus 100 for supporting a liquid sample 101 (see for example FIG. 1A or 1B). The primary X-ray beam is scattered at the sample and is diffracted to leave the sample along a direction 319 to be either detected by a WAXS-detector 355 or by a SAXS-detector 357. The two separate detectors 355 and 357, shown in FIG. 3, may also be combined in one continuous detector system, e.g. image plate or curved position sensitive detector. Not illustrated in FIG. 3 are data processing system and data storage system for processing and storing the intensity data of the diffracted or scattered X-ray beam from which information about the structure of substances and molecules within the liquid sample 101 may be derived.

We claim:

1. An apparatus for supporting a liquid sample for measuring an intensity of X-ray radiation scattered by the liquid sample, the apparatus comprising:
   a first support member having a first surface;
   a second support member having a second surface, the first surface and the second surface being adapted such that the liquid sample is supportable between the first surface and the second surface by a surface tension force,
   wherein the apparatus is configured such as to allow the X-ray radiation to impinge along a first direction through the first support member onto the liquid sample and to leave the liquid sample through the second member along a second direction different from the first direction to be detected by a detector,
   wherein the first member and/or the second member comprises an X-ray transparent window comprising diamond and/or silicon nitride,
   wherein the liquid sample contacts the first surface at a first wetted area of the first surface and contacts the second surface in a second wetted area of the second surface,
   wherein at least one of the first wetted area and the second wetted area is solventphilic, and
   a first surrounding area of the first surface is solventphobic around the first wetted area of that first surface and/or a second surrounding area of the second surface is solventphobic around the second wetted area of that second surface.

2. The apparatus according to claim 1, wherein the second direction and the first direction include an angle between 0.1° and 90°, between 2° and 60°, between 5° and 40° or between 7° and 35°.

3. The apparatus according to claim 1, wherein the first surface is a plane surface in at least a first region where the X-ray radiation impinges onto the first member and/or the second surface is a plane surface in at least a second region where the X-ray radiation leaves the second member.

4. The apparatus according to claim 1, wherein the first direction is transverse or perpendicular to at least one of the first surface and the second surface.

5. The apparatus according to claim 1, wherein the second surface has a larger area size than the first surface.

6. The apparatus according to claim 1, wherein the second surface is curved, concave or convex.

7. The apparatus according to claim 1, wherein the first wetted area of the first surface and the second wetted area of the second surface have a distance from each other between 0.1 mm and 3 mm, between 0.2 mm and 2 mm or between 0.5 mm and 1 mm.

8. The apparatus according to claim 7, further comprising a container wall enclosing a gas atmosphere, wherein the liquid sample comprises an annular surface between the first surface and the second surface in contact with the gas atmosphere.

9. The apparatus according to claim 8, further comprising a solvent vapor pressure/humidity control system for controlling a solvent vapor pressure/humidity of the gas atmosphere and/or comprising a temperature control system for controlling a temperature of the gas atmosphere and/or of the first support member and/or of the second support member.

10. The apparatus according to claim 9, wherein the container has an opening for sample loading or cleaning.

11. The apparatus according to claim 10, further comprising means for connecting the apparatus to a sample changer robot to allow for automatic exchange and/or cleaning of fluid samples in the apparatus.

12. A system for measuring an intensity of X-ray radiation scattered by a liquid sample, the system comprising:
   the apparatus according to claim 1; and
   a detector system configured for detecting the intensity of the X-ray radiation impinged along the first direction through the first support member onto the liquid sample and having left the liquid sample through the second member along the second direction.

13. The system according to claim 12, wherein the detector is adapted for detecting at least one of small angle X-ray scattering from the liquid sample and wide angle X-ray scattering from the liquid sample, resulting from the impingement of the X-ray radiation onto the liquid sample.

* * * * *